United States Patent [19]

Péron

[11] Patent Number: 4,665,031

[45] Date of Patent: May 12, 1987

[54] **CLONE OF THE SEA KALE (*CRAMBE MARITIMA L.*), AND PROCESS FOR VEGETATIVE PROPAGATION THEREOF**

[75] Inventor: Jean-Yves Péron, Angers, France

[73] Assignee: Ecole Nationale d'Ingenieurs des Travaux, Angers, France

[21] Appl. No.: 700,315

[22] Filed: Feb. 11, 1985

[30] Foreign Application Priority Data

Feb. 9, 1984 [FR] France .................. 84 01984

[51] Int. Cl.$^4$ .......................... C12N 5/00; A01B 79/00
[52] U.S. Cl. .................... 435/240; 435/241; 47/58
[58] Field of Search ............ Plt./89; 435/240, 241; 800/1

[56] References Cited

U.S. PATENT DOCUMENTS

4,038,778 8/1977 Kadkade ...................... 47/58
4,569,914 2/1986 Molnar et al. .................. 435/240

OTHER PUBLICATIONS

Flick et al. 1983 "Organogenesis" in *Handbook of Plant Cell Culture*, vol. 1, (Evans et al., eds.) pp. 13, 27, 28.
Bowes, 1976, "In vitro Morphogenesis of *Crambe maritima L.*" *Protoplasma*, v89, 185–188 (Abstract).

*Primary Examiner*—Lionel M. Shapiro
*Attorney, Agent, or Firm*—Fleit, Jacobson, Cohn & Price

[57] ABSTRACT

A method for the vegetative propagation of the sea kale species is described. Buds are obtained from in vitro neoformation on a callus, which in turn is obtained from fragments of petioles or leaf laminas of the plant. The rootless plants are then micropropogated in vitro in a plant culture medium and cytokinines in the absence of auxins. The rootless plants bearing one or two leaves are cultured in vitro in a plant growth broth and one or more auxins in the absence of cytokinins until roots develop. The rooted plants are transferred to a solid plant growth substrate and bred under conditions of a natural photoperiod of illumination until a plant is obtained which is capable of growth in the field.

18 Claims, 2 Drawing Figures

FIG. 1
FIG. 2

CLONE OF THE SEA KALE (*CRAMBE MARITIMA L.*), AND PROCESS FOR VEGETATIVE PROPAGATION THEREOF

The invention relates to a clone of the vegetable species CRAMBE which is not currently cultivated, obtained by neoformation in vitro on a callus of a petiole or lamina fragment removed from a plant of long-standing cultivation, and a method of vegetative propagation by micropropagation in vitro of the clone and the Crambe species.

The clone of Crambe obtained constitutes a new vegetable for the farmer and the consumer. Vegetative propagation, which makes use of in vitro techniques, makes it possible to produce, on a large scale and very homogeneously, cuttings to be placed in the field, and to provide for rapid launching of this new production.

DESCRIPTION

The invention relates to a clone of sea kale originating from a plant maintained in a conservatory since the 19th century, a fragment of which was subjected to organogenesis by culturing it in vitro, and also to a process for vegetative propagation thereof in vitro, leading to the production of cuttings which can be used by farmers.

The sea kale (*Crambe maritima* L.), which was probably cultivated to a small extent in France during the 19th century, has nowadays completely disappeared from the array of cultivated vegetables marketed in France, and in Europe. The description of this vegetable, as well as the main phytotechnical aspects of cultivating it, are described in several encyclopedic works on agronomy dating from the end of the 19th century (Vilmorin-Andrieux 1883, Nicholson 1895). In this plant species, which is found on sea coasts and is perennial by means of its rhizome, the young shoots in the etiolated state, on the resumption of growth in spring, form the edible organ. The use of root cuttings in the field is the method of propagation of the species and hence the traditional process for establishing a crop for this species.

On leaving the Ecole Nationale Superieure d'Horticulture of Versailles, where he held a post until August 1971, the present inventor took a sample of a rhizome fragment from a sea kale plant present in the departmental collection of edible plants at this establishment since the last century. The maintenance of this plant by successive fragmentation of the rhizome throughout generations without there being any modification of the plant from the standpoint of genotype—the description of the plant conforming with the description given by the above-mentioned authors—enables the inventor to assert that the plant referred to above was cultivated during the last century in the state in which it existed at the time the inventor removed the sample. Hence it cannot be of the same type as the wild crambe which we encounter in resorts on the coast of Brittany or Normandy. Since that date, the plant has been maintained in the botanical conservatory of the Department of Vegetable Crops of the Ecole Nationale d'Ingenieurs des Travaux Agricoles, Horticulture Section, of Angers, where the inventor is currently working.

From this parent plant, the inventor has created a clone according to the following process:

A fragment of an organ, which can be a petiole or lamina, is disinfected in a 10% strength NaOCl solution under vacuum for 10 minutes, rinsed in three washes of sterile water and cultured in test tubes in an air-conditioned room under the following conditions:

Temperature: day=24° C., night=18° C.

Light: 10,000 lux for 16 hours/24 hours.

The culture medium used has the following composition (amounts expressed per liter of culture medium):

| | |
|---|---|
| $NH_4NO_3$ | 0.48 g |
| $Ca(NO_3)_2.4H_2O$ | 0.71 g |
| $KNO_3$ | 0.15 g |
| KCl | 0.075 g |
| $MgSO_4.7H_2O$ | 0.493 g |
| $(NH_4)_2SO_4$ | 0.265 g |
| $KH_2PO_4$ | 0.140 g |
| $K_2HPO_4$ | 0.175 g |
| Fe EDTA(*) | 5 ml of stock solution |
| $H_3BO_3$ | 2.48 mg |
| $MnSO_4$ | 3.38 mg |
| $ZnSO_4$ | 1.15 mg |
| KI | 0.30 mg |
| $Na_2MoO_4$ | 0.10 mg |
| $CuSO_4$ | 0.05 |
| $CoSO_4$ | 0.05 mg |
| $NiSO_4$ | 0.05 mg |
| $AlCl_3$ | 0.05 mg |
| Glutamine | 200 mg |
| Adenine | 40 mg |
| Sucrose | 30 g |
| Agar C | 8 g |

(*)The stock solution of Fe EDTA (iron - ethylenediaminetetraacetic acid) is prepared in the following manner: 557 mg of $FeSO_4.7H_2O$ are mixed with 750 mg of $Na_2$ EDTA, and the volume of the mixture is adjusted to 100 ml with distilled water.

The pH of the above culture medium is adjusted to 5.6 with 1/10 HCl solution.

From these explants, calluses develop if an auxin, which can be indolacetic acid (0.2 to 0.7 mg/l, preferably 0.5 mg/l), and a mixture of cytokinins are added to the above medium in a suitable concentration ratio, for example, an auxin/cytokinin concentration ratio, expressed in mg/liter, of 0.066, the mixture of cytokinins also being in a suitable ratio, this mixture of cytokinins possibly consisting of, for example, kinetin (6 to 8 mg/l) and 6-benzylaminopurine (1 to 2 mg/l, preferably 1.5 mg/l), these two cytokinins also being in a suitable ratio, for example, in a concentration ratio (mg/l) of 4.

Under these conditions, organogenesis takes place in 20–28 days: there is neoformation of several buds on the calluses, and the buds then develop leaves. Each bud is then separated and then pricked out onto a so-called propagation medium according to the process explained below, which is also included in the present invention. The totality of the plants thus obtained, which have undergone subsequent pricking out onto a suitable rooting medium—which process also forms part of the invention—is homogeneous and formed of plants which are all identical to each other: this hence constitutes a clone of seal kale obtained according to the process explained above.

The characteristics of the plants of the clone thus obtained are collated below:

From the morphological standpoint, the plants of the clone possess leaves with a flattened lamina, the marginal notches of which, known as teeth and few in number, have a constant which is characteristic of all the plants in the clone and which can be designated by an index I defined as follows:

$$I = \frac{N}{I.s \times L}$$

I.s = length, expressed in cm, of the internerve space in question, enclosing a sinus (position of this space identical for all plants studied).

N = number of teeth present in the internerve space (I.s) in question.

L = total length of the lamina of the leaf, expressed in cm.

This index settles at an average value of 0.068.

The morphological homogeneity of the plants which form the clone created by the process described above is verified in terms of the index I by statistical analysis (determination of the standard deviation), as seen from the results which appear in Table I below:

TABLE I

| Plants | L (cm) | I.s (cm) | N | I |
|---|---|---|---|---|
| 1 | 24.9 | 5.1 | 6 | 0.047 |
| 2 | 31.6 | 9.1 | 20 | 0.069 |
| 3 | 37.5 | 12.5 | 40 | 0.085 |
| 4 | 31.9 | 8.9 | 24 | 0.084 |
| 5 | 39.5 | 7.4 | 20 | 0.068 |
| 6 | 34.4 | 5.5 | 12 | 0.063 |
| 7 | 37.5 | 9.7 | 19 | 0.052 |
| 8 | 23.0 | 5.5 | 10 | 0.079 |
| 9 | 18.5 | 3.2 | 4 | 0.067 |
| Average | | | | 0.068 |
| Standard deviation | | | | 0.014 |

Furthermore, the leaves (lamina + petiole) of the plants of the clone reach, when fully developed, an average length of 48 cm and are green due to the absence of anthocyanine pigments. Finally, for a suitable cultivation site, at whatever date they are planted, the plants originating from culture in vitro, according to the process which also forms part of the present invention, do not exhibit the floral state during the year when these plants were set up in the field after the micropropagation phase in vitro. When they resume growth in situ or in an air-conditioned chamber, the plants of the clone, after the first year of growth, develop, in darkness, shoots—the edible organ of the plant—which are of culinary value.

The invention also relates to a process for propagating the clone of sea kale which leads to the production of cuttings which can be used directly by farmers. The process can also be used on the sea kale species.

The buds originating from organogenesis in vitro, following the method according to the present invention described above, are separated from the callus under sterile conditions and then pricked out in a glass bowl containing 130 ml of a medium identical to the neoformation medium specified above except in respect of the nature of the growth substances and their balance: the mixture contains exclusively a cytokinin (e.g., 6-benzylaminopurine in a concentration of 6 to 8 mg/l, preferably 7 mg/l) or a mixture of cytokinins in a suitable ratio, for example, in a concentration ratio, expressed in mg/liter, of 1.66, this mixture of cytokinins possibly being kinetin (4 to 6 mg/l, preferably 5 mg/l) and 6-benzylaminopurine (2 to 4 mg/l, preferably 3 mg/l). The climatic conditions relating to the neoformation process are maintained in the present process. When all the conditions are observed, the buds induce lateral buds, the average number of which is 5, and which develop in 3 weeks, at the end of which a further pricking out will be necessary, with separation of the neoformed buds. This propagation process in vitro, which is also a subject of the present invention, enables 18,125 cuttings to be obtained after 18 weeks, starting from one neoformed bud.

When the requisite number of cutting-plants to be cultivated in the field is potentially reached, the buds are pricked out in vitro, in test tubes or in a glass bowl, on a so-called rooting medium the composition of which is identical to that of the neoformation or propagation medium with the exception of the growth substances which, in the present case, are represented exclusively by one or more auxins (e.g., naphthalene acetic acid in a concentration of, for example, 0.1 mg/l). The climatic conditions, which remain identical to the previous conditions, enable 3 to 4 white roots to be developed after 2 to 3 weeks.

The young plants thus obtained, equipped with 2 to 4 cm roots, are transferred to pots containing a non-sterilized, moistened substrate, this substrate possibly being composed of, for example, one-half yellow peat and one-half sand, and moistened to 80% of its water retention capacity. The pots are placed in mini-greenhouses equipped with an adjustable cover, under the following climatic conditions:

Day temperature: 20° C.

Night temperature: 15° C.

Natural illumination of the place where the intensity was maintained at less than 15,000 lux.

Maintained thus under these conditions, the plants develop both as regards their foliage (lamina approximately 10 cm for the oldest leaves) and as regards their root system (emission of three or four long, slightly tuberous roots, on which a fine and abundant lateral root-hair growth appears). After a 4 to 6 week breeding period, the plants can be transferred to the production field to set up production crops of the sea kale vegetable.

With the sea kale, the main advantages of vegetative micropropagation in vitro, compared to traditional propagation by root cuttings, are as follows:

complete homogeneity of the cuttings to be placed in the field, leading to very great homogeneity of the field crop, the propagation of an individual belonging to the clone can be carried out continuously, independently of the season and the climatic conditions, the micropropagation in vitro of sea kale makes it possible to increase dramatically the potential for production of cuttings starting from one individual, finally, it makes it possible to ensure for rapid launching of this new production by farmers.

FIGS. 1 and 2 illustrate plants obtained according to the invention.

What is claimed is:

1. A method of obtaining a bud from a sea kale organ comprising:
   (a) obtaining a fragment from the organ; said organ selected from the group consisting of petioles and leaf laminas;
   (b) in vitro culturing said fragment in a volume of a culture medium comprising an amount of an auxin and a mixture of cytokinins wherein the ratio of auxin to cytokinins is about 0.066; said fragment being cultured under a light and for a time effective to develop a callus;

(c) culturing said callus in said medium for a period of time sufficient to permit the development of a bud; and (d) separating said bud from said callus.

2. The method of claim 1, wherein the culture medium comprises the following composition per liter:

| | |
|---|---|
| $NH_4NO_3$ | about 0.48 g, |
| $Ca(NO_3)_2.4H_2O$ | about 0.71 g, |
| $KNO_3$ | about 0.15 g, |
| $KCl$ | about 0.075 g, |
| $MgSO_4.7H_2O$ | about 0.493 g, |
| $(NH_4)_2SO_4$ | about 0.265 g, |
| $KH_2PO_4$ | about 0.140 g, |
| $K_2HPO_4$ | about 0.175 g, |
| Fe EDTA | about 5 ml of stock solution, |
| $H_3BO_3$ | about 2.48 mg, |
| $MnSO_4$ | about 3.38 mg, |
| $ZnSO_4$ | about 1.15 mg, |
| KI | about 0.30 mg, |
| $Na_2MoO_4$ | about 0.10 mg, |
| $CuSO_4$ | about 0.05 mg, |
| $CoSO_4$ | about 0.05 mg, |
| $NiSO_4$ | about 0.05 mg, |
| $AlCl_3$ | about 0.05 mg, |
| Glutamine | about 200 mg, |
| Adenine | about 40 mg, |
| Sucrose | about 30 g, |
| Agar C | about 8 g; | wherein the stock solution of Fe(EDTA) comprises 557 mg of $FESO_4.7H_2O$ and 75 mg of $Na_2EDTA$ in a final volume of water of 100 ml, the pH being adjusted to about 5.6.

3. The method of claim 1 wherein the auxin is present in an amount of between about 0.2 mg/l and about 0.7 mg/l.

4. The method of claim 1 wherein the cytokinins are kinetin and 6-benzylaminopurine and are present in an amount of between about 6 mg/l and about 8 mg/l and about 1 mg/l and about 2 mg/l, respectively; the ratio of kinetin/6-benzylaminopurine being about 4.

5. The method of claim 1 wherein the amount of light is about 10,000 lux and the plant is illuminated for about 16 hours every 24 hours.

6. The method of claim 1 wherein said fragment is cultured for between about 20 days and about 28 days.

7. A method of obtaining multiple buds from a sea kale organ, comprising the method of claim 1, and further comprising:

(e) pricking out said bud and transferring said pricked bud into a volume of a growth medium comprising a cytokinin or a mixture of cytokinins in the absence of auxins, effective to promote growth;

(f) culturing said pricked buds in said growth medium for a period of time sufficient to permit the growth of lateral buds; and (g) separating said lateral buds; wherein steps (e) through (g) are performed at least once.

8. The method of claim 7 wherein the cytokinin in step (e) is 6-benzylaminopurine and is present in an amount of between about 6 mg/l and about 8 mg/l.

9. The method of claim 7 wherein the mixture of cytokinins in step (e) contains between about 4 mg/l and about 6 mg/l of kinetin and about 2 mg/l and about 4 mg/l 6-benzylaminopurine; the ratio of kinetin/6-benzylaminopurine being about 1.66.

10. The method of claim 7 wherein said step (f) is conducted for about 3 weeks.

11. A method of homogeneous propagation of sea kale, comprising:

(a) obtaining a sea kale organ bud;

(b) placing said bud in a volume of a propagation medium comprising the following composition per liter of propagation medium:

| | |
|---|---|
| $NH_4NO_3$ | about 0.48 g, |
| $Ca(NO_3)_2.4H_2O$ | about 0.71 g, |
| $KNO_3$ | about 0.15 g, |
| $KCl$ | about 0.075 g, |
| $MgSO_4.7H_2O$ | about 0.493 g, |
| $(NH_4)_2SO_4$ | about 0.265 g, |
| $KH_2PO_4$ | about 0.140 g, |
| $K_2HPO_4$ | about 0.175 g, |
| Fe EDTA | about 5 ml of stock solution, |
| $H_3BO_3$ | about 2.48 mg, |
| $MnSO_4$ | about 3.38 mg, |
| $ZnSO_4$ | about 1.15 mg, |
| KI | about 0.30 mg, |
| $Na_2MoO_4$ | about 0.10 mg, |
| $CuSO_4$ | about 0.05 mg, |
| $CoSO_4$ | about 0.05 mg, |
| $NiSO_4$ | about 0.05 mg, |
| $AlCl_3$ | about 0.05 mg, |
| Glutamine | about 200 mg, |
| Adenine | about 40 mg, |
| Sucrose | about 30 g, |
| Agar C | about 8 g; | wherein the stock solution of Fe(EDTA) comprises 557 mg of $FeSO_4.7H_2O$, and 750 mg of $Na_2EDTA$ in a final volume of water of 100 ml, the pH being adjusted to about 5.6 and an amount of an auxin or mixtures thereof in the absence of cytokinins under a light and for a time effective to develop a root;

(c) transferring said rooted buds onto a solid plant growth substrate in the presence of water; and (d) cultivating said rooted buds illuminated with a light, at a temperature and for a time sufficient to develop a plant.

12. The method of claim 11 wherein the auxin in step (b) is naphthalene acetic acid and is present in an amount of about 0.1 mg/l.

13. The method of claim 11 wherein step (b) is allowed to proceed for about between 2 and 3 weeks.

14. The method of claim 11 wherein step (c) is conducted when the bud roots are between about 2 cm and about 4 cm long.

15. The method of claim 11 wherein step (d) is conducted for a time sufficient for the plant to develop leaves about 10 cm long and about three tuberous roots having fine hairs.

16. The method of claim 15 wherein step (d) is conducted for about between 4 weeks and 6 weeks.

17. A method of vegetative propagation of sea kale, comprising:

(a) obtaining a fragment of a seal kale organ selected from the group consisting of petioles and leaf lamines;

(b) in vitro culturing said fragment in a volume of a culture medium comprising the following composition per liter:

| | |
|---|---|
| $NH_4NO_3$ | about 0.48 g, |
| $Ca(NO_3)_2.4H_2O$ | about 0.71 g, |
| $KNO_3$ | about 0.15 g, |
| $KCl$ | about 0.075 g, |
| $MgSO_4.7H_2O$ | about 0.493 g, |
| $(NH_4)_2SO_4$ | about 0.265 g, |
| $KH_2PO_4$ | about 0.140 g, |
| $K_2HPO_4$ | about 0.175 g, |
| Fe EDTA | about 5 ml of stock solution, |

-continued

| | |
|---|---|
| H$_3$BO$_3$ | about 2.48 mg, |
| MnSO$_4$ | about 3.38 mg, |
| ZnSO$_4$ | about 1.15 mg, |
| KI | about 0.30 mg, |
| Na$_2$MoO$_4$ | about 0.10 mg, |
| CuSO$_4$ | about 0.05 mg, |
| CoSO$_4$ | about 0.05 mg, |
| NiSO$_4$ | about 0.05 mg, |
| AlCl$_3$ | about 0.05 mg, |
| Glutamine | about 200 mg, |
| Adenine | about 40 mg, |
| Sucrose | about 30 g, |
| Agar C | about 8 g; | wherein the stock solution of Fe(EDTA) comprises 557 mg of FeSO$_4$.7H$_2$O, and 750 mg of Na$_2$EDTA in a final volume of water of 100 ml, the pH being adjusted to about 5.6, and an amount of a mixture of an auxin and a mixture of cytokinins; said fragment being cultured under light and for a time effective to develop a callus;

(c) culturing said callus in said medium for a period of time sufficient to permit the development of a bud;

(d) separating said bud from said callus;

(e) placing said bud in a volume of propagation medium comprising an amount of an auxin or mixtures of auxins in the absence of cytokinins under a light and for a time, effective to develop a root;

(f) transferring said rooted buds onto a solid plant growth substrate in the presence of water; and (g) cultivating said rooted buds under a light, at a temperature and for a time sufficient to develop a plant.

18. The method of claim 17 further comprising between steps (d) and (e), the following steps:

(I) pricking out said bud and transferring said pricked bud into a volume of a growth medium comprising an amount of a cytokinin or a mixture of cytokinins in the absence of auxins effective to promote growth;

(II) culturing said pricked buds in said growth medium for a period of time sufficient to permit the growth of lateral buds; and (III) separating said lateral buds; wherein steps (I) through (III) are performed at least once.

* * * * *